United States Patent
Welch et al.

(10) Patent No.: US 6,342,160 B2
(45) Date of Patent: *Jan. 29, 2002

(54) METHOD FOR SCREENING CHROMATOGRAPHIC ADSORBENTS

(76) Inventors: Christopher J. Welch, 229 Greenfield, Glenview, IL (US) 60025; Marina Protopopova, 525 W. Hawthorne Pl., Chicago, IL (US) 60601; Bhat Ganapati, 799 Oak Meadow Ct., Grayslake, IL (US) 60030

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/226,941

(22) Filed: Jan. 8, 1999

Related U.S. Application Data

(60) Provisional application No. 60/070,887, filed on Jan. 9, 1998.

(51) Int. Cl.[7] ............................................. B01D 15/08
(52) U.S. Cl. .................... 210/635; 210/656; 210/198.2; 436/161
(58) Field of Search ................................ 210/635, 656, 210/659, 198.2; 436/161; 422/70

(56) References Cited

U.S. PATENT DOCUMENTS

| | | | | |
|---|---|---|---|---|
| 4,243,753 A | * | 1/1981 | Regnier | 210/198.2 |
| 4,579,663 A | * | 4/1986 | Poile | 210/656 |
| 4,719,017 A | * | 1/1988 | Uchino | 210/656 |
| 5,203,992 A | * | 4/1993 | Drouen | 210/198.2 |
| 5,209,853 A | * | 5/1993 | Lynch | 210/198.2 |
| 5,409,611 A | * | 4/1995 | Kauver | 210/656 |
| 5,422,004 A | * | 6/1995 | Pirkle | 210/198.2 |
| 5,443,734 A | * | 8/1995 | Fetner | 210/656 |
| 5,487,831 A | * | 1/1996 | Pirkle | 210/656 |
| 5,491,096 A | * | 2/1996 | Sportsman | 210/656 |
| 5,670,054 A | * | 9/1997 | Kibbey | 210/656 |
| 5,679,582 A | * | 10/1997 | Bowie | 436/518 |
| 5,766,481 A | * | 6/1998 | Zambias | 210/656 |
| 5,770,087 A | * | 6/1998 | Reuter | 210/198.2 |
| 5,827,946 A | * | 10/1998 | Klee | 210/656 |
| 5,938,931 A | * | 8/1999 | Ono | 210/656 |
| 5,939,612 A | * | 8/1999 | Wylie | 210/656 |
| 6,054,047 A | * | 4/2000 | Hindsgaul | 210/656 |
| 6,068,766 A | * | 5/2000 | Van Davelaar | 210/656 |

OTHER PUBLICATIONS

Snyder, Introduction to Modern Liquid Chromatography, John Wiley & Sons, New York, 1979, pp. 595–597 and 731–732.*

Francotte, J. Chromotgr. 686 (1996) pp. 77–83.*

* cited by examiner

Primary Examiner—Ernest G. Therkorn
(74) Attorney, Agent, or Firm—McDonnell Boehnen Hulbert & Berghoff

(57) ABSTRACT

The invention discloses a method for rapid identification of a candidate selective separation material by placing small samples of the candidate material in an array of vials and adding a solution of the analytes to be separated. The solution is allowed to interact or equilibrate and the distribution of the analytes in the solid or liquid phase is measured usually by gas or liquid chromatography. The identified candidate material with the greatest differential adsorption of the analytes is selected and used as an adsorbent for large scale separation. The rapid screening of chromatographic adsorbents provides an efficient way of finding suitable absorbent materials for large scale separations.

19 Claims, 17 Drawing Sheets expanded view showing candidate selector immobilized on solid phase particles expanded view showing candidate selector immobilized on solid phase particles Expanded view showing mixture of two analytes in supernatant solution expanded views showing:

↑
depletion of circular
analytes in supernatant

↑
enrichment of circular
analytes in solid phase

| CSP | k'₁ | α | k'₁ | α | k'₁ | α | k'₁ | α |
|---|---|---|---|---|---|---|---|---|
| Commercial | 2.17 | 1.20 | 5.67 | 1.10 | 3.19 | 1.33 | 1.21 | 1.39 |
| SPS | 2.30 | 1.15 | 6.48 | 1.08 | 3.64 | 1.33 | 1.26 | 1.33 |

Figure 6
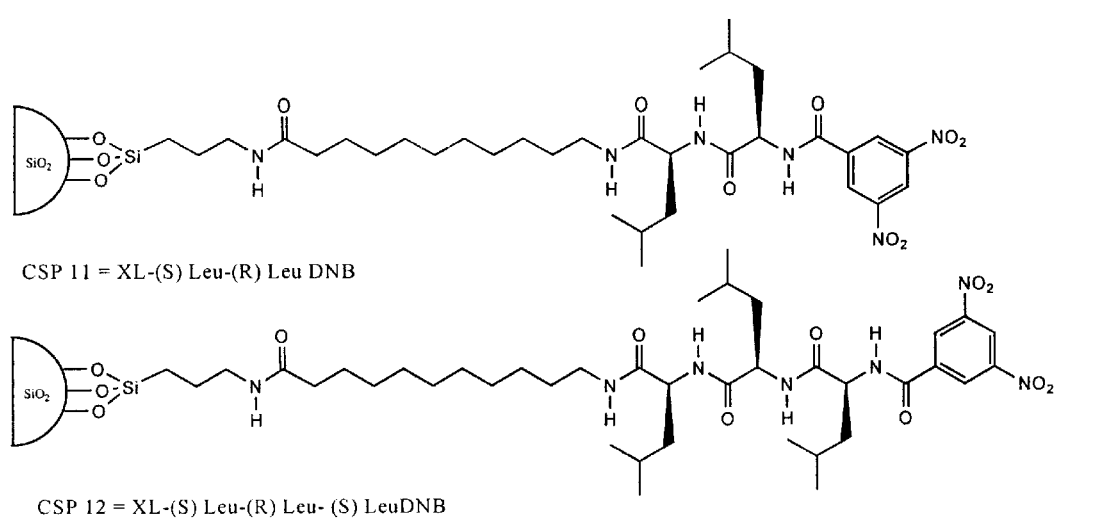
CSP 11 = XL-(S) Leu-(R) Leu DNB
CSP 12 = XL-(S) Leu-(R) Leu- (S) LeuDNB
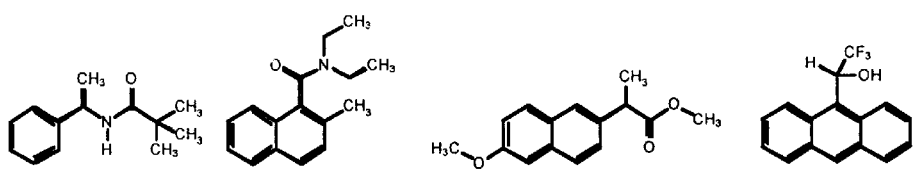
| CSP | k'₁ | α | k'₁ | α | k'₁ | α | k'₁ | α |
|---|---|---|---|---|---|---|---|---|
| 11 | 2.25 | 1.16 | 2.20 | 1.22 | 1.32 | 1.00 | 2.37 | 1.20 |
| 12 | 1.70 | 1.00 | 3.15 | 2.22 | 8.06 | 1.84 | 4.83 | 1.36 |

Figure 7
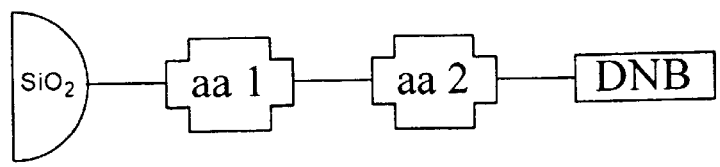
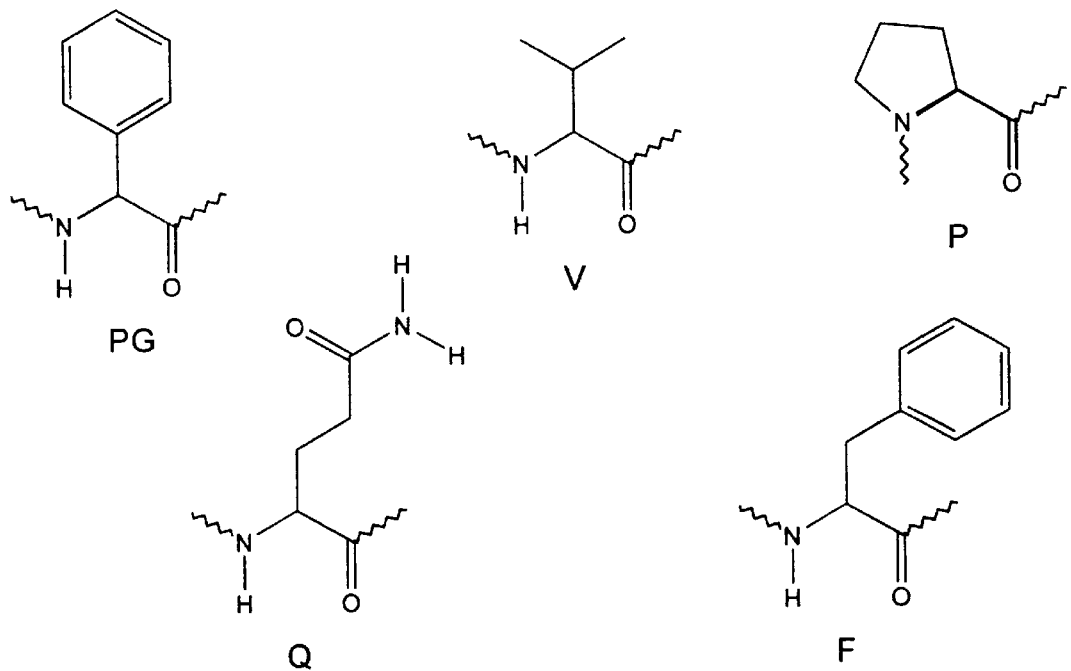
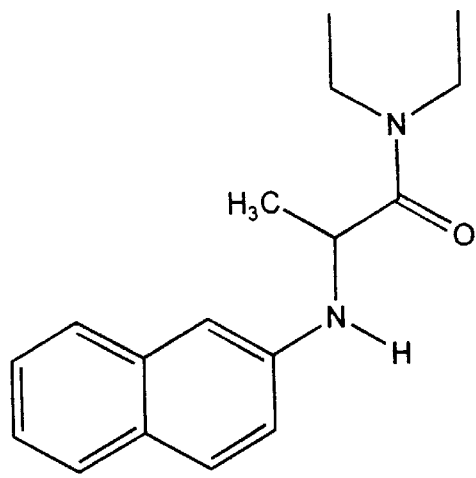
test racemate, 1 mobile phase = 20% IPA/hexane; flow rate = 2.0 ml/min; UV 280 nm

Figure 12
Preparative Separation Using Analytical Column - 100 mg Injection
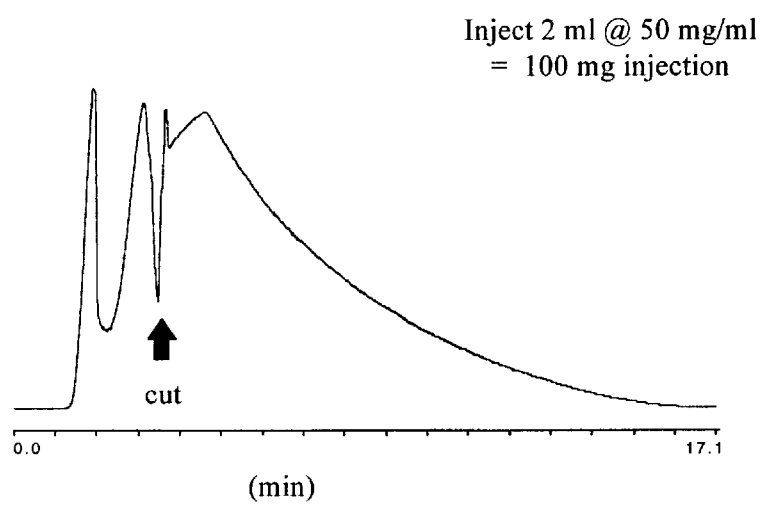
Conditions: mobile phase = ethyl acetate; flow rate = 2.0 ml/min; detection = UV 380 nm
Analysis of Fractions from 100 mg Injection on Analytical Column
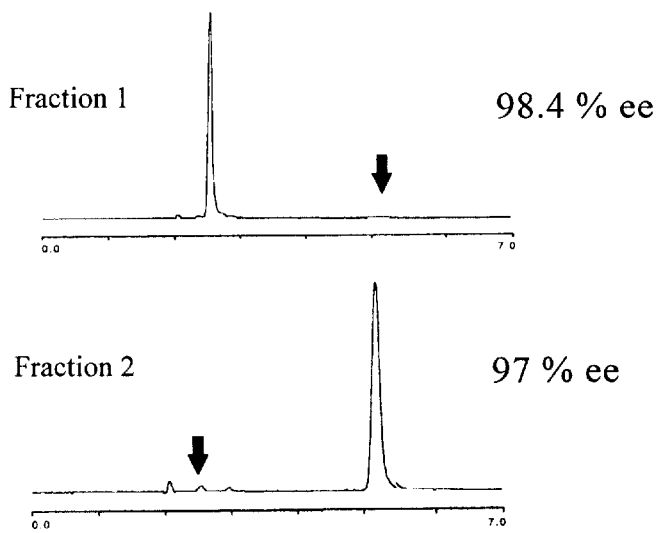
Conditions: Column = (S) DNB Leu CSP (4.6 mm x 25 cm); mobile phase = MeOH; flow rate = 1.5 ml/min; detection = UV 254 nm

Figure 13

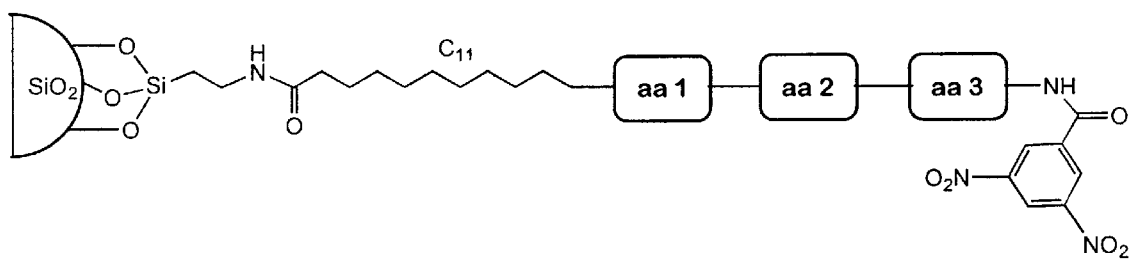

Four libraries of DNB tripeptides (144 total) were prepared via solid phase synthesis on silica and used for screening with naproxen as free acid (4 x 10-5 M solution in 2% IPA/Hexane + 0.1% of AcOH)

Leucine library, 36 CSPs: aa1 = (S)-Leu, aa2 and aa3 = (S)- and (R)-Leu, (S)- and (R)-Phg, (S)-and (R)-Asn

Phenylglycine libary, 36 CSPs: aa1 = (S)-Phg, aa2 and aa3 = (S)- and (R)-Leu, (S)- and (R)-Phg, (S)-and (R)-Asn

Asparagine libary, 36 CSPs: aa1 = (S)-Asn, aa2 and aa3 = (S)- and (R)-Leu, (S)- and (R)-Phg, (S)-and (R)-Asn

Proline libary, 36 CSPs: aa2 = (S)-Pro, aa1 and aa3 = (S)- and (R)-Leu, (S)- and (R)-Phg, (S)-and (R)-Asn mobile phase = 80:20:0.5 hexane/IPA/HOAc; flow rate = 2.0 ml/min; UV 265 nm

Figure 17
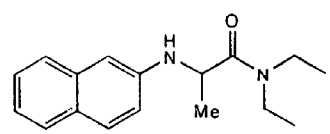
Test racemate 1
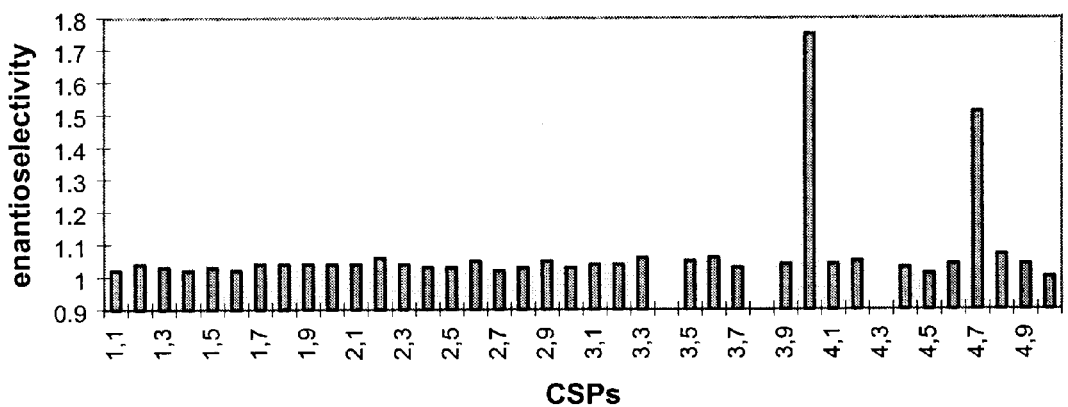
Screening of *(S)*-Leucine benzamides with test racemate 1.
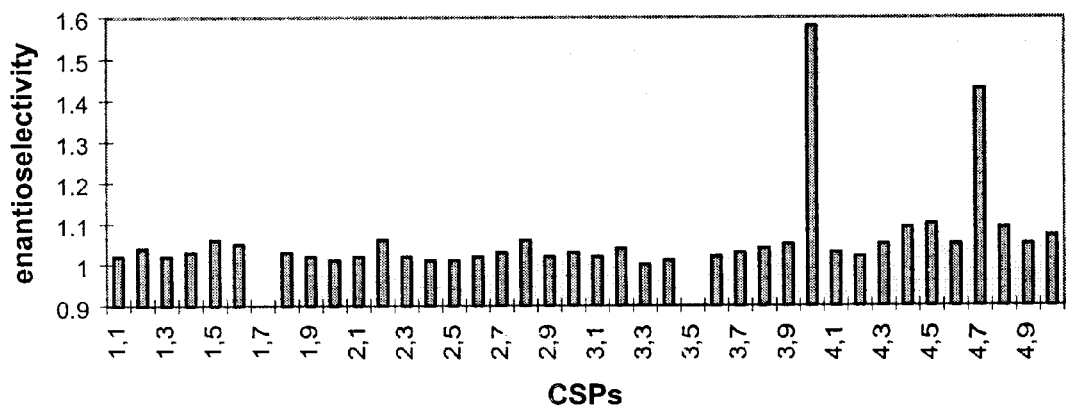
Screening of *(S)*-Phenylglycine benzamides with test racemate 1.

METHOD FOR SCREENING CHROMATOGRAPHIC ADSORBENTS

This application claims the priority of Provisional Application No. 60/070,887 filed Jan. 9, 1998.

BACKGROUND OF THE INVENTION

1. Field of the Invention

The invention relates to the field of separation of molecules using selective adsorbents.

2. DESCRIPTION OF THE ART

Since its discovery by Tswett nearly a century ago, the technique of adsorption chromatography has evolved into a tool of fundamental importance to the biological and chemical sciences. Early chromatographers employed readily available adsorbents such as calcium carbonate, sugar, starch, paper, wool, silk, alumina and silica to perform an impressive variety of separations. Today, researchers with a problem separation are faced with a variety of adsorbents from which to choose. Furthermore, additional adsorbents can readily be prepared using combinatorial chemistry approaches. As a general rule, the more selective adsorbents allow for more economical chromatographic separations, with simple and inexpensive batch adsorption separations becoming possible with extremely selective adsorbents. A means of rapidly finding the most selective adsorbent for a given separation task is needed.

One area where the development of highly selective adsorbents is of great importance is the large scale separation of enantiomers using chiral stationary phases (CSPs). The current selection of commercial chiral stationary phases (CSPs) for large scale chromatographic separations is rather limited, and most have been developed as general purpose CSPs rather than the best CSP for a particular separation. While new CSPs can be designed, the development time is often too long to merit serious consideration by process engineers.

Within the past decade the technique of chromatographic enantioseparation has become the method of choice for analytical determinations of enantiopurity. Allenmark, Chromatographic Enantioseparation: Methods and Applications, Ellis Horwood, N.Y., 1991. The method is widely used, particularly in the pharmaceutical industry where most new chiral drugs are manufactured in enantiomerically pure form. In recent years the use of preparative chromatographic enantioseparation has become increasingly popular. While generally more expensive than manufacturing routes employing enantioselective synthesis or classical resolution, chiral HPLC offers a considerable advantage of speed. Consequently, many pharmaceutical companies use preparative chiral HPLC in the early stages of drug discovery to rapidly produce enantiomerically pure drug candidates for animal testing, metabolism and toxicology studies, etc. Once a drug candidate has been selected for larger scale development, alternative manufacturing methods are often used, although in a few cases chiral HPLC is used to produce enantiopure drugs on large scale.

Most commercial CSPs have been developed using trial and error methodology, and have been commercialized because they demonstrate some general ability to separate enantiomers. Of these many commercial CSPs, only a small fraction are available in bulk or can be produced in an economical fashion for large scale preparative chromatography. Francotte, E., *J. Chromatogr.*, 666, 565–601, 1994. Furthermore, rather than a CSP which has a general ability to separate the enantiomers of a large number of racemates, the process engineer considering a potential manufacturing route for an enantiopure drug is interested in a CSP which can separate the enantiomers of one particular compound.

Practical large scale chromatographic enantioseparation requires highly enantioselective CSPs. For example, chromatographic resolution of the enantiomers of a racemate using a CSP with an enantioselectivity of 1.3 can be rather tedious. A comparable CSP having an enantioselectivity of 2 can sometimes afford 5–10 fold greater productivity.

SUMMARY OF THE INVENTION

The present invention relates to a process for screening candidate selective adsorbents for differential adsorption of two or more chemical components. In this process a solid phase consisting of the candidate adsorbent is allowed to contact a solution phase containing the component or components of interest. Interaction or equilibration of material in the solution phase with the stationary phase of the selective adsorbent results in a change of concentration of the analyte or analytes in both the stationary phase and solution phase. This change in concentration can be measured by a variety of techniques and gives an indication of the degree of adsorption of the analyte by the stationary phase. Thus, small amounts of candidate selective adsorbents are placed in an array of containers and a solution of the chemical compounds to be separated is added to each container. The components are allowed to interact or equilibrate with the selective adsorbent and the amount of each component in the solution phase or in the solid phase of the array of containers is measured. The adsorbent showing the greatest differential adsorption for the chemical components is identified as being potentially useful for large scale separations. The invention is particularly useful in identifying selective adsorbents for enantiomer separations.

BRIEF DESCRIPTION OF THE FIGURES

FIG. 6 illustrates substantial differences in the performance of structurally similar dipeptide and tripeptide CSPs.

FIG. 7 illustrates five amino acids used to prepare a library of 50 dipeptide DNB CSPs and the test racemate, 1, used for evaluation.

FIG. 12 shows preparative HPLC separation of the enantiomers of the test racemate, 1, using the column from FIG. 11.

FIG. 13 illustrates four libraries of DNB tripeptide CSPs.

FIG. 17 illustrates the results of the screening of two of the acyl amino acid libraries from FIG. 16 for enantioselective recognition of test racemate, 1. In both instances, 3,5-dinitrobenzamide and 4-methyl, 3,5-dinitrobenzamide are shown to be superior to other acyl groups.

DESCRIPTION OF THE PREFERRED EMBODIMENTS

The invention encompasses a method whereby candidate selective adsorbents can be rapidly evaluated for their potential for carrying out the separation of a mixture of two or more chemical components. Using this method, libraries containing small amounts of about 1 mg to 100 mg of many different candidate adsorbents can be rapidly evaluated using automated equipment. This approach dramatically decreases the time required to find a suitable selective adsorbent for a given separation. The method is useful for finding adsorbents which can be used for the analytical or preparative chromatographic separation of enantiomers, the separation of impurities from pharmaceuticals or other products, the separation of fermentation products from their associated impurities or any process in which two or more compounds are separated by a chromatography or any process which relies upon differential adsorption of two or more chemical species. The method has the added advantage that the compound mixture for which a separation is desired can be used directly without the need for separations, purifications, radiolabeling or other chemical derivatization.

Figure 1:
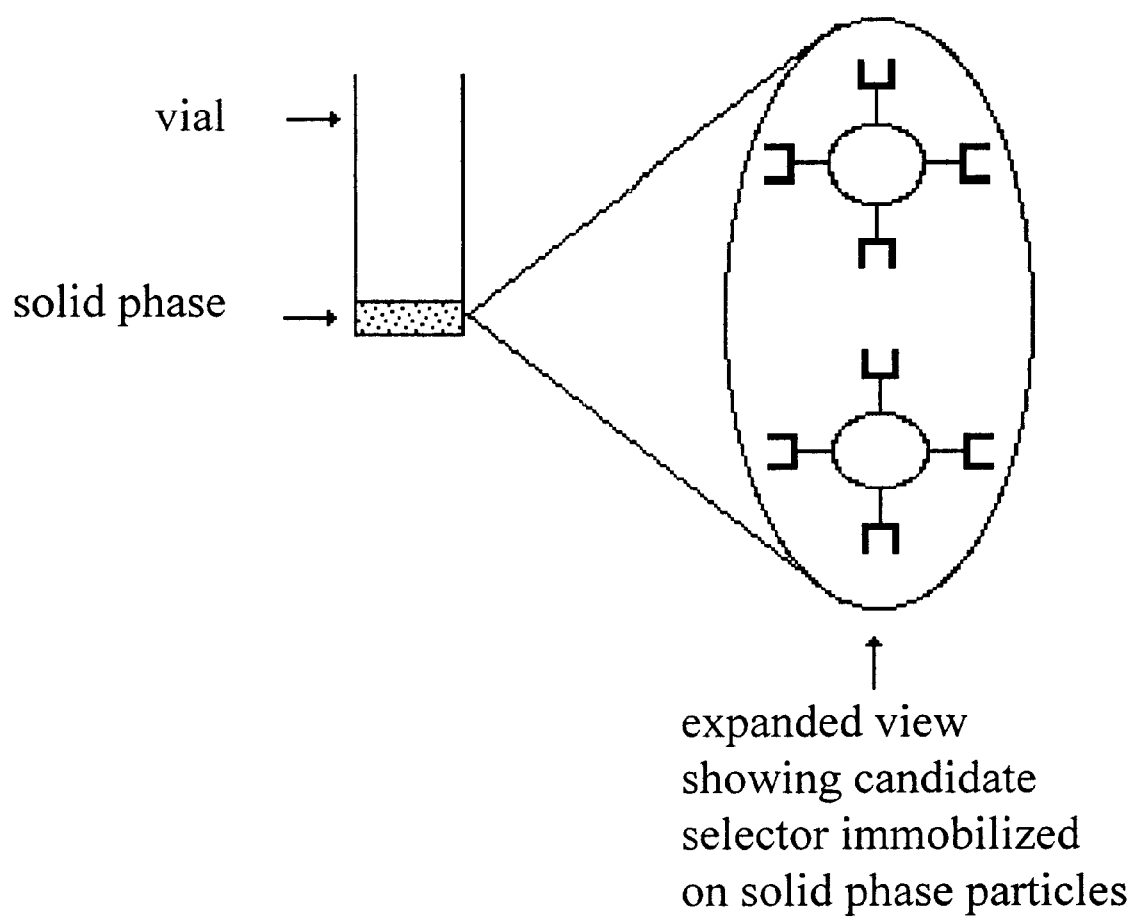
FIG. 1 is an expanded view of the solid phase prior to equilibration.

The screening process is depicted schematically in the figures which follow. A small amount of a candidate absorbent is placed in a vial or similar receptacle (FIG. 1). The expanded view of the candidate absorbent shows two particles containing four pendant selectors each. Any number of particles can be used, and in contrast to chromatography, the performance of the assay does not require the use of very small and regular particles. Indeed, there are some advantages to be found in the use of large particles or even a single bead. For example, since larger particles tend to settle more rapidly and completely, the use of large particles allows the supernatant solution to be sampled without risk of particles clogging the syringe.

In the case where a solid phase material which preferentially binds one enantiomer is desired (e.g. a chromatographic chiral stationary phase) the preferred method involves adding a solution of the racemic mixture to the candidate chromatographic adsorbents and measuring the enantioenrichment of either the solution phase or the stationary phase using chromatographic techniques such as chiral HPLC, HPLC/MS, GC, CE or spectroscopic techniques such as NMR with chiral solvating agents or NMR analysis of diastereomeric derivatives or chiroptical spectroscopic techniques such as CD or polarimetry. An alternative method of performing the assay could involve analysis of a nonracemic solution of the target analyte or could involve independently measuring the degree of complexation of each enantiomer.

Figure 2:
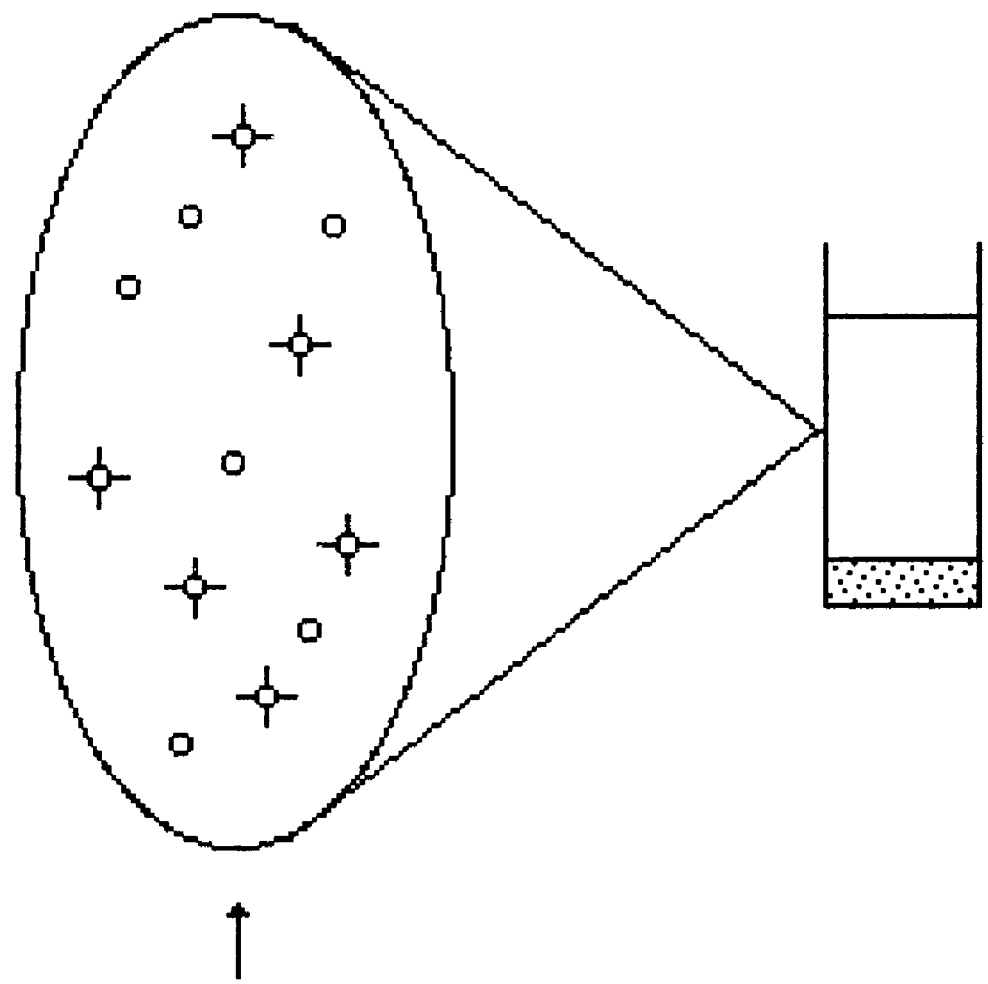
FIG. 2 is an expanded view of the liquid phase prior to equilibration.

A dilute solution containing known relative concentrations of the mixture of the analytes of interest is then added (FIG. 2). In this example, two analytes are represented as circles and crosses. It is important that the analyte solution be of low enough concentration to prevent saturation of the adsorption sites on the chromatographic adsorbent. In addition, the polarity of the solution phase should be such that the target molecules are neither completely adsorbed nor completely free in solution. Equilibration or interaction of the material in the liquid phase with the chromatographic adsorbent may result in the preferential binding of one of the analytes in the mixture to the chromatographic adsorbent, resulting in a depletion of that analyte in the solution phase.

Figure 3:
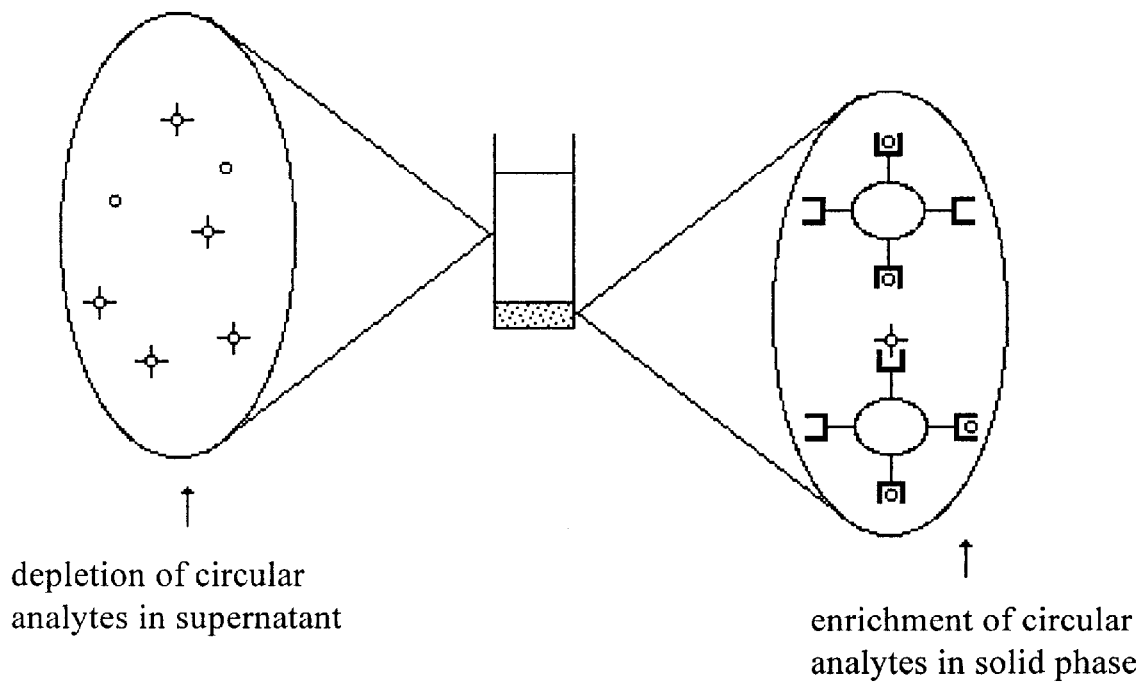
FIG. 3 is a view of the liquid and solid phase after equilibration.

Analysis of the relative abundance of the analytes in either the solid phase or the solution phase gives some indication of the degree of selectivity of the adsorbent-analyte interaction. In the case illustrated here, a strong preference for adsorption of the circular analyte is depicted. Those adsorbents which show the highest degrees of selectivity are likely candidates for a chromatographic stationary phase which may be capable of separating the mixture of chemical components in question, FIG. 3.

This technique has several advantages over previous methods of evaluating candidate selective adsorbents. Only a small amount, about 1 mg to 100 mg, of the candidate adsorbent is used in an assay, and this material need not be packed into a column or capillary for evaluation. Furthermore, the candidate adsorbent can be washed free of all chemical components and reused. The target analytes can be used directly without any need for purifications, resolutions, or synthetic operations. A variety of analytical techniques can be used to measure the relative abundance of the analyte molecules in either the solid phase or the solution phase. The process is not limited to mixtures of two analytes, but could conceivably be used to screen for e.g., an adsorbent which would show preferential adsorption of a single desired product from a complex mixture containing a number of different associated impurities. Similarly, the technique could conceivably be used to search for an adsorbent which would preferentially adsorb the various impurities from this same complex mixture while only weakly adsorbing the desired product. The screening process is rapid, and is amenable to automation, which allows for high throughput screening of libraries of new candidate chromatographic adsorbents prepared using solid phase diversity-generating synthetic approaches.

A variety of analytical tools can be used to determine the relative concentrations of the analytes in the solid phase. For example, analysis of the relative concentrations of the analytes in the liquid phase can be performed using chromatographic techniques such as HPLC, HPLC/MS, SFC, CE or GC or spectroscopic techniques such as NMR or chiroptical techniques such as CD or any analytical technique or chemical process capable of showing the absolute or relative concentrations of the analytes in question.

Determination of the relative concentrations of the analytes in the solid phase can be done by a variety of methods.

The extent of enrichment in the solid phase is typically greater than that in the supernatant solution. However, these measurements are often more difficult, usually requiring a filtration or other phase separation before the determination of the relative concentration of materials adsorbed onto the solid phase can be determined. A convenient method for determining the relative concentration of the analytes in the solid phase simply involves removal of the supernatant layer by rapid suction filtration, followed by the addition of a solvent which liberates most of the adsorbed material from the solid phase, followed by analysis of the resulting supernatant solution by HPLC or other analytical techniques mentioned above.

Those skilled in this art will recognize that a wide variety of solid polymeric or inorganic particles may be functionalized to form candidate selective adsorbents using techniques and procedures which are known from the fields of solid phase synthesis and combinatorial chemistry. Such particles bearing pendant groups such as amine, carboxylic acid, hydroxyl, halide, aldehyde, or thiol may be used for attachment of one or more molecular fragments to provide a large number of candidate selective adsorbents. Further, by linking enantiopure moieties to functionalized solid particles, a large number of candidate CSPs and CSP libraries can be prepared.

Suitable candidate adsorbents are made by techniques described in the following examples or can be purchased from Regis Technologies, Inc., 8210 Austin Avenue, Morton Grove, Ill. 60053-0519.

EXAMPLE 1

Silica-Based Solid Phase Synthesis.

Modified solid phase peptide synthesis on aminopropyl silica particles was chosen as a preferred method for preparing combinatorial libraries of CSPs.

Silica-Based Solid Phase Synthesis of DNB-Leu CSP

Figure 4:
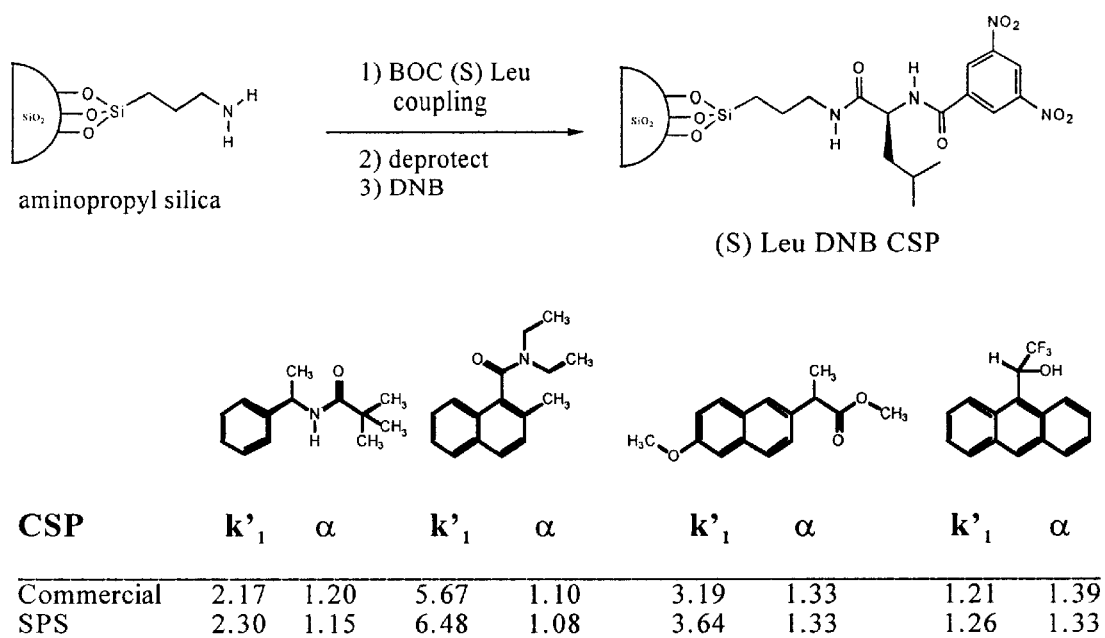
FIG. 4 shows that the performance of the DNB Leu CSP prepared by solid phase synthesis is comparable with the performance of the commercial version of this CSP.

As a model study, the well known 3,5-dinitrobenzoyl Leucine (DNB-Leu) CSP was prepared on 5 g scale using the solid phase synthesis protocol outlined in FIG. 4. The CSP thus obtained was packed in a column which separated a group of test analytes nearly as well as the commercial column.

Silica-Based Solid Phase Synthesis of DNB-Peptido CSPs

Figure 5:
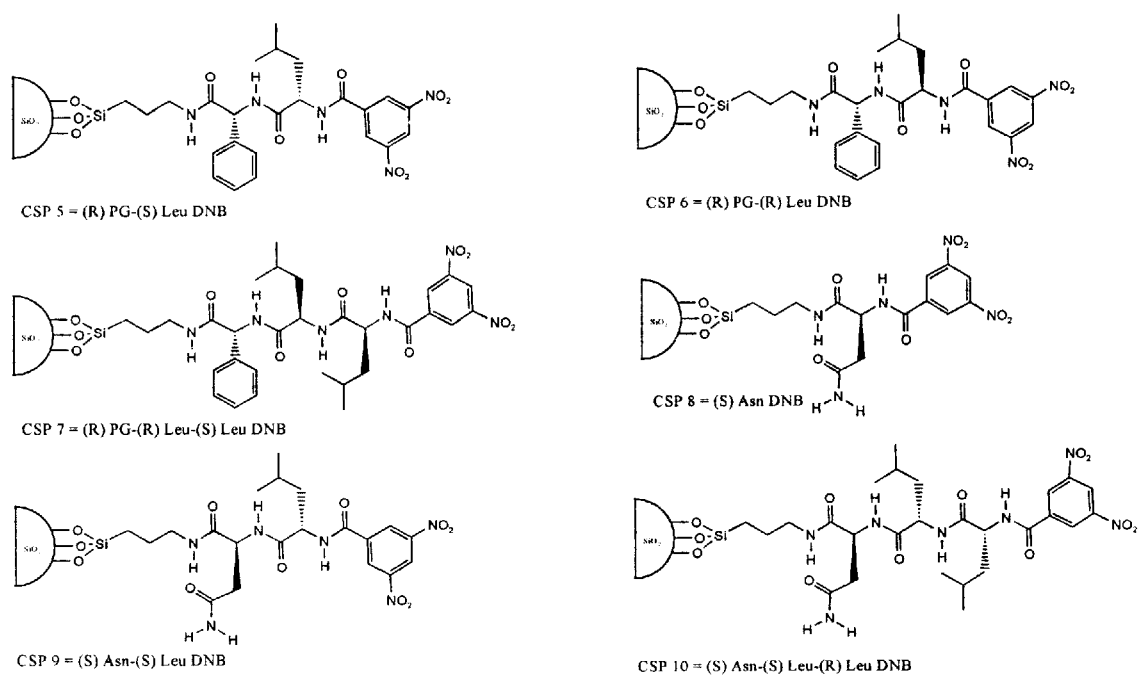
FIG. 5 shows a variety of DNB-peptido CSPs prepared by solid phase synthesis.

Preparing and evaluating a group of peptido CSPs using a split synthesis was conducted in a manner analagous to that shown in FIG. 4. A representative sampling of some of the CSPs which were made and evaluated is shown in FIG. 5. Each CSPs was prepared on 5 g scale, packed into a column and evaluated chromatographically. Two additional CSPs from this initial group are shown in FIG. 6. These CSPs are nearly identical, differing only in one leucine residue. Nevertheless, substantial differences in enantioselectivity are noted for the group of test analytes.

Microscale Silica-Based Solid Phase Synthesis of CSPs

The foregoing experiments show the utility of a silica based solid phase synthesis approach to CSP development. While the cost and time required to make each of these materials on 5 g scale is less than that of conventional CSP development, an even more rapid way of sampling the structural diversity of the DNB peptide family was required. Consequently, candidate CSPs on 50 mg scale were prepared and screened ex-column to evaluate the enantioselectivity of each CSP.

A library of 50 dipeptide DNB CSPs were prepared using combinations of the 5 amino acids; valine, glutamine, phenylalanine, phenylglycine and proline (FIG. 7). This set includes sterically bulky, strong hydrogen bonding and aromatic amino acids.

The solid phase peptide synthesis which was used in the multigram scale preparation of the CSPs shown in FIGS. 5 and 6 was scaled down to prepare 50 mg of each of 50 dipeptide DNB CSPs resulting from combinations of the 5 amino acids shown in FIG. 7.

Evaluation of CSP Library

Figure 8:
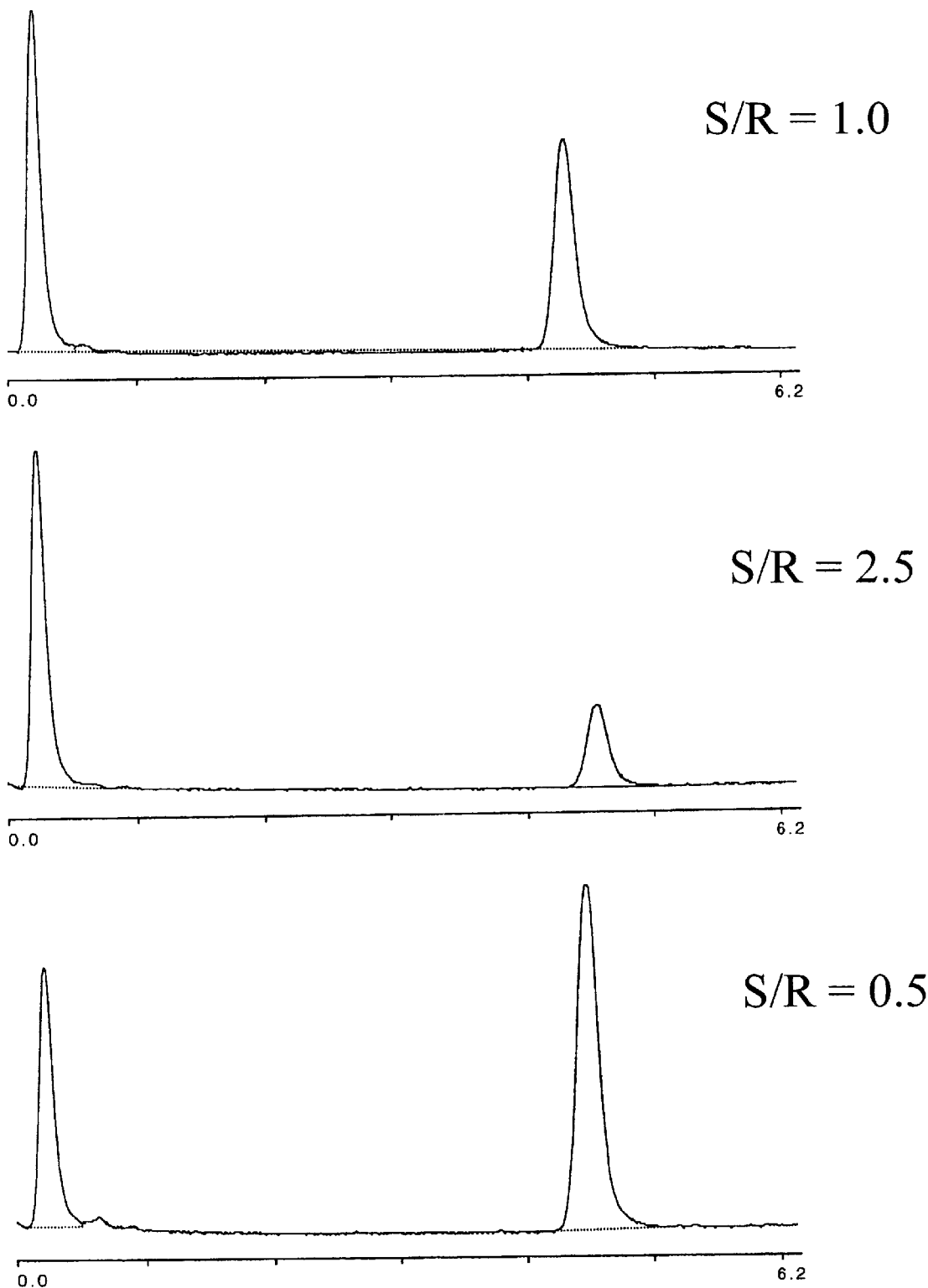
FIG. 8 shows three representative screening chromatograms including the blank (no CSP), a CSP which strongly adsorbs the (R) enantiomer of the test racemate, 1, and a CSP which strongly adsorbs the (S) enantiomer of the test racemate, 1.
Figure 9:
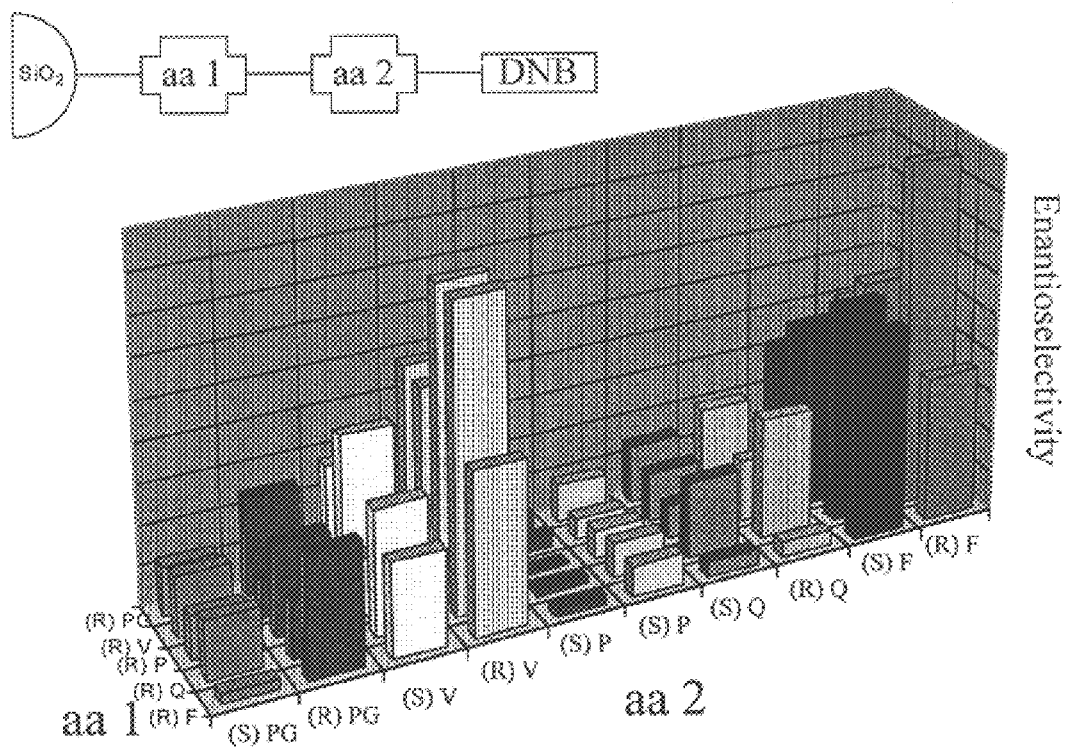
FIG. 9 shows the results of a screening of a library of 50 dipeptide DNB CSPs for the separation of the enantiomers of test racemate, 1.

The CSP library was first evaluated using the test racemate, 1. The evaluation procedure consists of adding 1 ml of a $1 \times 10^{-5}$ M solution of the test racemate in 20% IPA/hexane to each of the 50 CSP-containing vials. The vials were then capped and transferred to an HPLC autosampler, where they were allowed to sit for a period of 30 min. HPLC analysis of 50 $\mu$l of the supernatant solution from each vial was performed using a 46×250 mm (S) DNB-Leucine CSP operating at a flow rate of 1 ml/min with a mobile phase of methanol and detection at 254 nm. Three representative chromatograms are shown in FIG. 8, including the blank (no CSP), a CSP which strongly adsorbs the (R) enantiomer of the test racemate, and a CSP which strongly adsorbs the (S) enantiomer of the test racemate. The results of the screen are presented in FIG. 9. The vertical axis in FIG. 9 represents enantioselectivity, with the tallest bars indicating the most enantioselective CSPs. The overall method provides useful information on the separation capability of each material. Previous experience with this chiral recognition system had led us to believe that an amide hydrogen on the amino acid closest to the DNB group (aa 2) is essential for good separation. Furthermore, it was suspected that amino acids with a large steric group at this position should work best, with aromatic groups at this position generally being poorer than steric groups. It thus comes as no surprise that the proline in position aa 2 works very poorly, while valine and phenylalanine in this position work best. Some unexpected results are obtained, even though this chiral recognition system has been extensively studied for more than a decade by a variety of techniques in addition to chromatography, including X-ray analysis of co-crystals and nOe NMR analyses of 1:1 complexes. One unexpected result of the screen is the finding that glutamine in position aa 1 seems to have a beneficial effect on enantioselectivity.

Preparation and Evaluation of a Focused CSP Library

Figure 10:
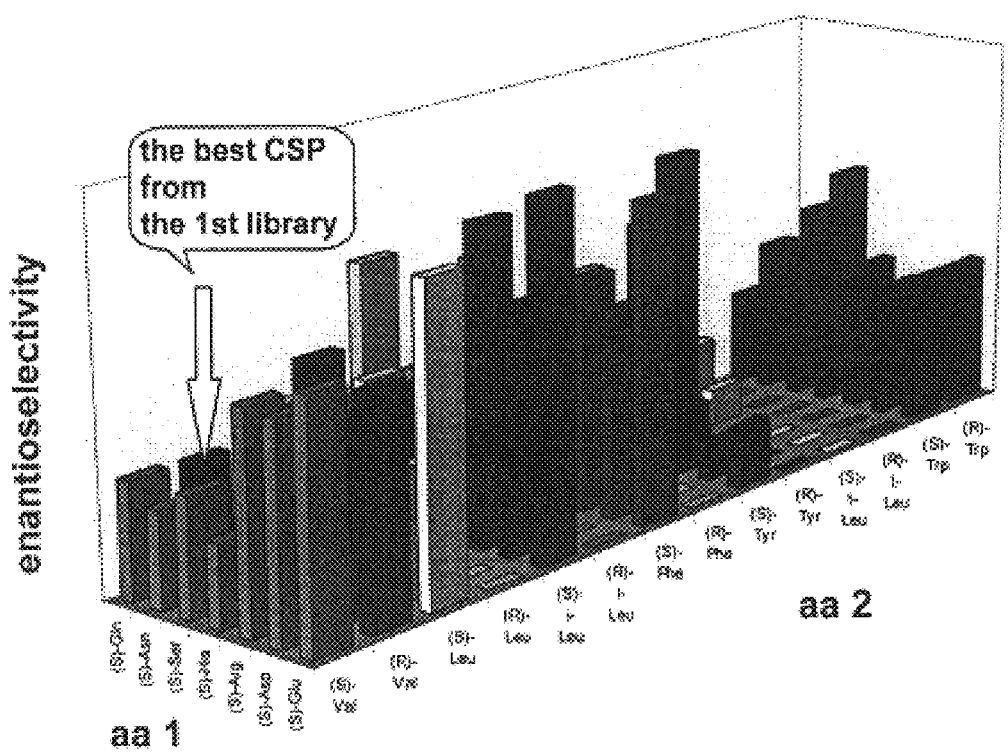
FIG. 10 shows results of a screening of a focused library of dipeptide DNB CSPs containing hydrogen-bonding sidechains in the aa 1 position and sterically bulky sidechains in the aa 2 position. Many of these second generation CSPs are superior to the best CSPs in the library shown in FIG. 9.

This initial screen provides a basis for further optimization for this chiral recognition system. The initial screen indicates that DNB dipeptide CSPs having a strong hydrogen bonding sidechain in the aa 1 position and a sterically bulky sidechain in the aa 2 position work best for the test analyte. A focused library based on this motif was prepared and evaluated. As shown in FIG. 10, many of the members of this new library show superior enantioselectivity to the DNB Val-Gln CSP, which was the best CSP in the initial library.

Selection, Scale-Up and Evaluation of an 'Optimal' CSP

Figure 11:
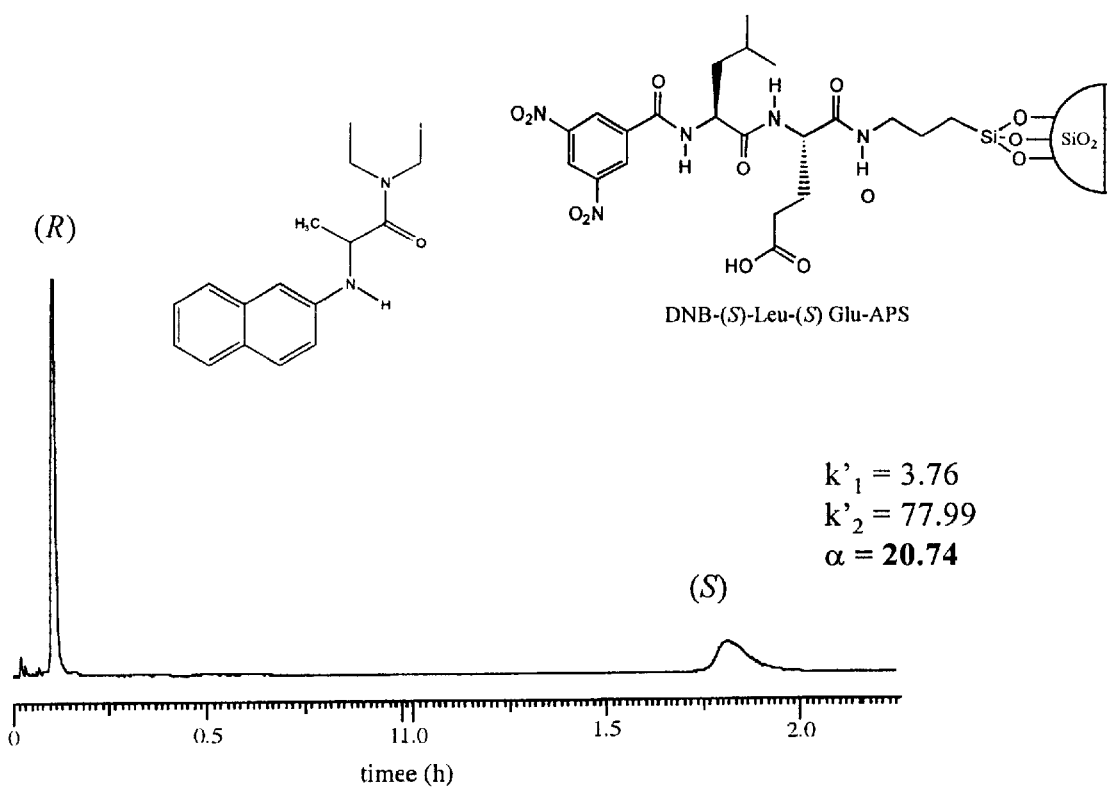
FIG. 11 shows a separation of the enantiomers of test racemate, 1, using a conventional 4.6×250 mm analytical HPLC column containing one of the best dipeptide DNB CSPs from FIG. 10.

One of the preferred CSPs shown in FIG. 10 was prepared on 5 g scale and packed into 4.6×250 mm HPLC column for evaluation. As shown in FIG. 11, this HPLC column was shown to separate the enantiomers of the test analyte, 1, with an enantioselectivity in excess of 20. This HPLC column was shown to be highly effective for the preparative separation of the enantiomers of the test analyte, 1, as shown in FIG. 12. In this example, near baseline resolution of enantiomers is observed, even with a single injection of 100 mg of racemate. Analysis of the two fractions from this preparative separation shows that the collected enantiomers are isolated in a highly enantioenriched form. Furthermore, the relatively rapid separation time permits a very high preparative throughput.

This example illustrates the utility of the technology for the discovery of a highly selective adsorbent for a given separation problem.

EXAMPLE 2

Figure 14:
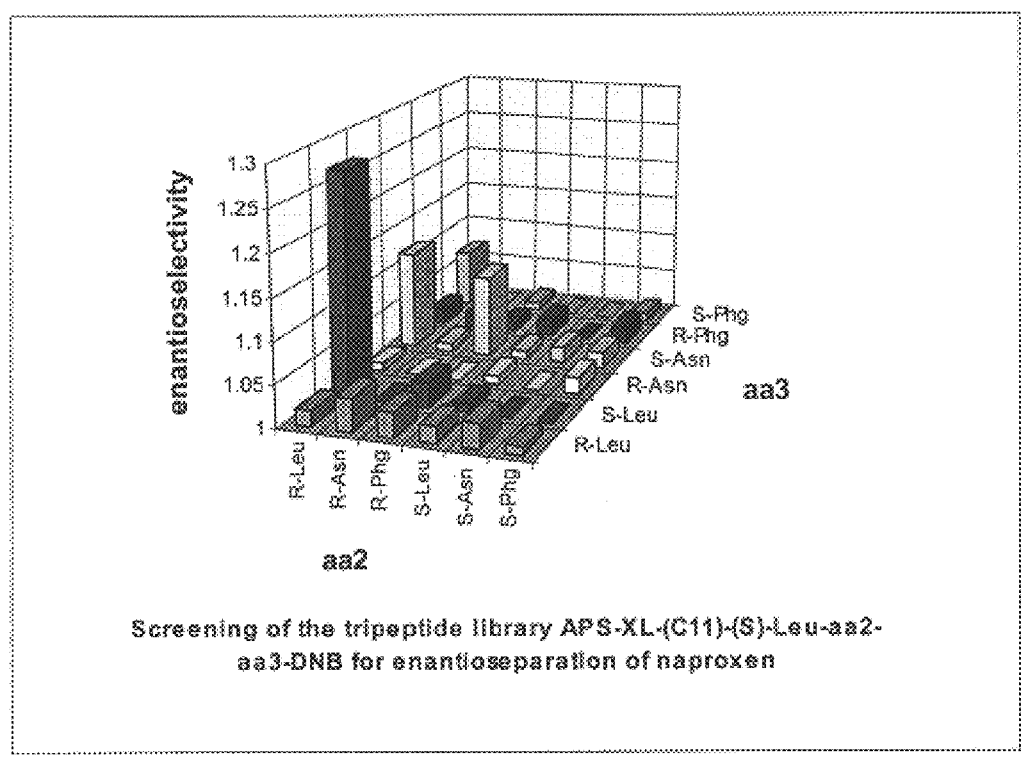
FIG. 14 illustrates the results of the screening of leucine library from FIG. 13 for enantioselective naproxen recognition.
Figure 15:
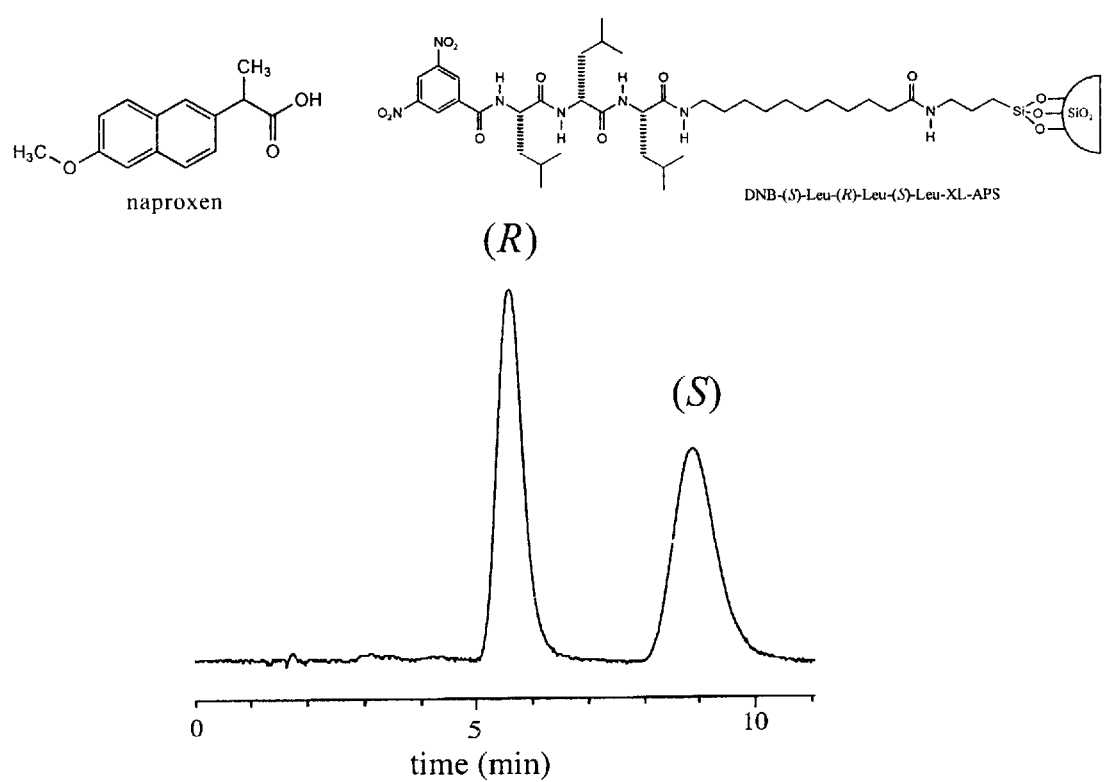
FIG. 15 illustrates chromatographic separation of the enantiomers of the drug, naproxen, using the best CSP indicated by the CSP library screening shown in FIG. 14.

Using an approach analogous to that described in Example 1, a series of tripeptide DNB CSPs were prepared and evaluated. Four such libraries of 36 CSPs each were prepared by analogous solid phase synthesis techniques and are shown in FIG. 13. Evaluation of this CSP library as candidate adsorbents for separation of the enantiomers of the drug, naproxen, revealed several promising library members, as shown in FIG. 14. FIG. 15 shows the evaluation of the best CSP indicated by the library screening shown in FIG. 14 using a 4.6×250 mm HPLC column.

EXAMPLE 3

Figure 16:
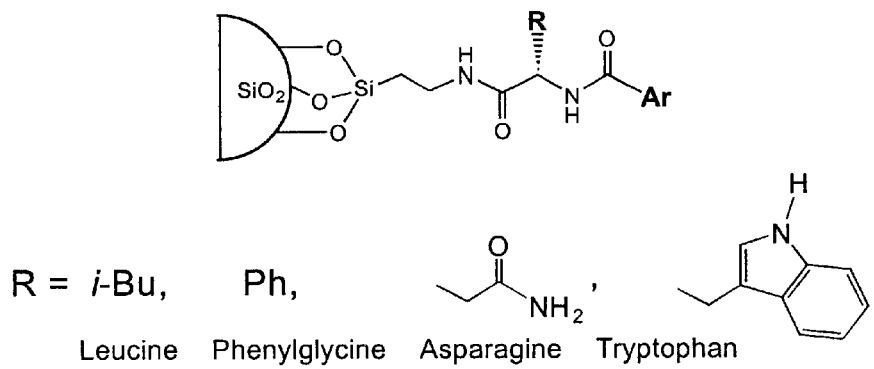
FIG. 16 illustrates libraries of acyl amino acid CSPs comprised of four different amino acids each acylated with 40 different carboxylic acids.

Using an approach analogous to that described in Example 1, the series of acyl amino acid CSPs shown in FIG. 16 were prepared. Several different BOC amino acids were coupled with aminopropylsilica, followed by deprotection to afford the corresponding CSPs bearing a free terminal amino group. These CSPs were next transferred to individual vials, where they were coupled with each of a group of 40 different carboxylic acids. The resulting library of acyl amino acid derived CSPs was screened for ability to separate the enantiomers of the test racemate, 1. The results of the screens for two such sub-libraries are shown in FIG. 17. These results emphasize the fact that 3,5 dinitrobenzamide groups works well for separation of the enantiomers of test racemate, 1.

EXAMPLE 4

This example illustrates that the technique is not limited to CSP libraries on a silica surface. We have prepared and evaluated a subset of the library illustrated in FIG. 9 using polystyrene based media. In this example, Chiron SynPhase™ Crowns (PS Crown Type:I series: aminomethylated) were used to prepare several CSPs in the dipeptide DNB series. Evaluation of the resulting Crown CSPs showed results which were similar to those found in Example 1, although some differences were noted. The use of polystyrene as a solid phase may be of some use for the preparation of adsorbent libraries owing to the fact that many types of solid phase synthesis are possible on polystyrene or other media which are not possible with silica. Furthermore, existing solid phase libraries can be accessed and evaluated as candidate adsorbents.

EXAMPLE 5

Several members of the CSP library described in Example 1 were evaluated for their ability to selectively adsorb the enantiomers of the test racemate, 1, using HPLC with MS detection. The evaluation procedure was the same as that described in Example 1, except that HPLC evaluation was performed using a 46×250 mm (R) DNB-Phenylglycine CSP operating at a flow rate of 1 ml/min with a mobile phase of 1:1:1 methanol/acetonitrile/water with detection by mass spectrometry. This detection method was shown to afford essentially the same information obtained using UV detection, and in other cases where the analyte under investigation has poor UV absorbance, HPLC with MS detection has proven to afford the requisite sensitivity and reliability for direct screening of the CSP libraries.

EXAMPLE 6

An indirect chemical derivatization method was used to evaluate several CSP libraries for their ability to separate the enantiomers of a racemic secondary amine which had poor UV absorbance and was not well separated by chiral HPLC. A $10^{-4}$ M solution of the racemic secondary amine in 5% IPA/hexane was added to a group of vials, each containing about 50 mg of a different candidate CSPs on a porous silica support. After waiting for one hour, 500 $\mu l$ of supernatant solution was withdrawn from each vial and transferred to a fresh autosampler vial. 3,5-dinitrobenzoyl chloride (5.5× $10^{-7}$ moles) and diisopropylethylamine chloride ($6\times10^{-7}$ moles) were then added to each vial. After two hours of reaction, the contents of each vial was analyzed using an autosampler HPLC system with UV detection.

These examples illustrate the invention and are not intended to limit in spirit or scope.

What is claimed is:

1. A method for identifying a selective adsorbent for separating analyte mixtures without the use of columns or capillary systems, comprising:
   a. providing an array of containers each having a candidate selective adsorbent;
   b. adding a solution of the analyte mixture to be separated to each selective adsorbent candidate in the containers, said solution added to the containers in a concentration whereby said adsorbents are not saturated and having a polarity whereby the analytes are neither completely adsorbed nor completely free in solution;
   c. allowing the analyte mixture to interact with the selective adsorbent candidate;
   d. identifying the distribution of analyte mixture in the solution or on the selective adsorbent candidate, said identifying step being carried out in said containers without removal of the selective adsorbent candidate to a column or capillary system.

2. The method of claim 1 wherein the selective adsorbent is silica having an organic molecule covalently linked thereto.

3. The method of claim 2 wherein the selective adsorbent is derived from silica having an aminoalkyl group covalently linked thereto.

4. The method of claim 3 wherein the aminoalkyl group has at least one enantioenriched amino acid covalently linked thereto.

5. The method of claim 1 wherein the amount of selective adsorbent is about 1 mg to 100 mg.

6. The method of claim 1 wherein the analyte mixture is tested in an array of 50–1000 candidate selective adsorbents.

7. The method of claim 1 wherein the distribution of analytes is measured by high pressure liquid chromatography or gas chromatography.

8. The method of claim 7 wherein chromatographic detection by mass spectrometry is employed.

9. The method of claim 7 wherein an aliquot of the analyte mixture is removed and subjected to chemical derivatization prior to analysis.

10. The method according to claim 1 wherein the analyte mixture is a mixture of enantiomers.

11. The method of claim 1 wherein the distribution of analytes is measured by a chiroptical spectroscopy technique.

12. The method of claim 11 wherein the chiroptical spectroscopy technique is circular dichroism spectroscopy.

13. The method of claim 11 wherein the chiroptical spectroscopy technique is measurement of optical rotation.

14. The method of claim 1 further comprising the following step:

e. determining a relative concentration of analyte remaining in said solution by using techniques selected from the group consisting of chromatographic techniques selected from the group, consisting of HPLC, HPLC/MS, SFC, CE, GC, spectroscopic techniques selected from the group consisting of NMR, NMR with chiral solvating agents and NMR analysis of diastereomeric derivatives, and chiroptical spectroscopic techniques.

15. The method of claims 14 wherein the chiroptical spectroscopy technique is circular dichroism spectroscopy.

16. The method of claim 14 wherein the chiroptical spectroscopy technique is polarimetry.

17. The method of claim 1 further comprising the following step:

e. removing said solution from one or more containers;

f. adding a solvent capable of liberating adsorbed analyte from said candidate selective adsorbent to obtain a supernatant solution including said solvent and said analyte;

analyzing said supernatant solution to determine a relative concentration of analyte adsorbed by said candidate selective adsorbent, said analysis obtained by using techniques selected from the group consisting of HPLC, HPLC/MS, SFC, CE, GC, spectroscopic techniques selected from the group consisting of NMR, NMR with chiral solvating agents and NMR analysis of diastereomeric derivatives, and chiroptical spectroscopic techniques.

18. The method of claim 17 wherein the chiroptical spectroscopy technique is circular dichroism spectroscopy.

19. The method of claim 17 wherein the chiroptical spectroscopy technique is polarimetry.

* * * * *